United States Patent [19]
James et al.

[11] Patent Number: 6,008,008
[45] Date of Patent: Dec. 28, 1999

[54] ESCULETIN DERIVATIVES

[75] Inventors: Arthur James, Jesmond; Lyle Armstrong, Ashington, both of United Kingdom

[73] Assignee: IDG (UK) Limited, Manchester, United Kingdom

[21] Appl. No.: 09/184,231

[22] Filed: Nov. 2, 1998

[30] Foreign Application Priority Data

May 1, 1996 [GB] United Kingdom .................... 9609024

[51] Int. Cl.$^6$ .............................. C12Q 1/04; C12Q 1/54; C12Q 1/00

[52] U.S. Cl. .................................. 435/34; 435/14; 435/4; 514/27; 514/23; 514/25; 514/237.5; 514/451; 514/457; 536/17.2; 536/17.9; 536/18.1

[58] Field of Search ................................. 435/34, 14, 4; 514/27, 23, 25, 237.5, 451, 457; 536/17.2, 17.9, 18.1

[56] References Cited

U.S. PATENT DOCUMENTS

| | | | |
|---|---|---|---|
| 5,055,594 | 10/1991 | Mize ........................................ | 549/223 |
| 5,455,268 | 10/1995 | Watanable et al. ...................... | 514/457 |
| 5,574,062 | 11/1996 | Hashimoto et al. ..................... | 514/457 |
| 5,731,293 | 3/1998 | Watanable et al. ....................... | 514/27 |

FOREIGN PATENT DOCUMENTS

| | | |
|---|---|---|
| 0 122 148 A1 | 10/1984 | European Pat. Off. . |
| 0 614 896 A1 | 9/1994 | European Pat. Off. . |
| Wo 94/24119 | 10/1994 | WIPO . |

OTHER PUBLICATIONS

Albert, A. et al., "The Influence of Chemical Constitution on Anti–Bacterial Activity. Part VI: The Bactericidal Action of 8–Hydroxyquinoline (Oxine)," *Brit. J. Exp. Pathol.* 34:119–130 (1953).

Ballantyne, M.M. et al., "Claisen Rearrangements–II. Synthesis of Six Natural Coumarins," *Tetrahedron* 27:871–877 (1971).

Berg, J.D. and L. Fiksdal, "Rapid Detection of Total and Fecal Coliforms in Water by Enzymatic Hydrolysis of 4–Methylumbelliferone–β–D–Galactoside," *Appl. Environ. Microbiol.* 54:2118–2122 (1988).

Brenner, K.P. et al., "New Medium for the Simultaneous Detection of Total Coliforms and *Echerichia coli* in water," *Appl. Environ. Microbiol.* 59:3534–3544 (1993).

Brodsky, M.H. and D.A. Schiemann, "Evaluation of Pfizer Selective Enterococcus and KF Media for Recovery of Fecal Streptococci from Water by Membrane Filtration," *Appl. Environ. Microbiol.* 31:695–699 (1976).

Cenci, G. et al., "Comparison of flurogenic and conventional membrane filter media for enumerating coliform bacteria," *Microbios* 76:47–54 (1993).

Daoust, R.A. and W. Litsky, "Pfizer Selective Enterococcus Agar Overlay Method for the Enumeration of Fecal Streptococci by Membrane Filtration," *Appl. Microbiol.* 29:584–589 (1975).

Edberg, S.C. et al., "Rapid Spot Test for the Determination of Esculin Hydrolysis," *J. Clin. Microbiol.* 4:180–184 (1976).

Greene, T.W., "Benzyl Ethers," in: *Protective Groups in Organic Synthesis,* Wiley–Interscience Publication, New York, NY, pp. 97–99 (1981).

James, A.L. and P. Yeoman, "Detection of Specific Bacterial Enzymes by High Contrast Metal Chelate Formation. Part I. 8–Hydroxyquinoline–β–D–Glucoside, an Alternative to Aesculin in the Differentiation of Members of the Family Enterobacteriaceae," *Zbl. Bakt. Hyg. A* 267:188–193 (1987).

James, A.L., "Enzymes in Taxonomy and Diagnostic Bacteriology," in: *Chemical Methods in Prokaryotic Systematics,* Goodfellow, M. and A.G. O'Donnell, eds., John Wiley & Sons, New York, NY, pp. 471–492 (1994).

James, A.L. et al., "Note: Cyclohexenoesculetin–β–D–glucoside: a new substrate for the detection of bacterial β–D–glucosidase," *J. Appl. Microbiol.* 82:532–536 (1997).

Kodaka, H. et al., "Evaluation of New Medium with Chromogenic Substrates for Members of the Family Enterobacteriaceae in Urine Samples," *J. Clin. Microbiol.* 33:199–201 (1995).

Lowe, G.H., "The Rapid Detection of Lactose Fermentation in Paracolon Organisms by the Demonstration of β–D–Galactosidase," *J. Med. Lab. Technol.* 19:21–25 (1962).

Manafi, M. et al., "Flurogenic and Chromogenic Substrates Used in Bacterial Diagnostics," *Microbiol. Rev.* 55:335–348 (1991).

Plovins, A. et al., "Use of Fluorescein–Di–β–D–Galactopyranoside (FDG) and $C_{12}$–FDG as Substrates for β–Galactosidase Detection by Flow Cytometry in Animal, Bacterial, and Yeast Cells," *Appl. Environ. Microbiol.* 60:4638–4641 (1994).

Swan, A., "The Use of a Bile–Aesculin Medium and of Maxted's Technique of Lancefield Grouping in the Identification of Enterococci (Group D Streptococci)," *J. clin. Pathol.* 7:160–163 (1954).

Trepeta, R.W. and S.C. Edberg, "Esculinase (β–glucosidase) for the rapid estimation of activity in bacteria utilizing a hydrolyzable substrate, p–nitrophenyl–β–D–glucopyranoside," *Antonie van Leeuwenhoek* 53:273–277 (1987).

International Search Report for International Application No. PCT/GB97/01202, mailed Oct. 27, 1997.

*Primary Examiner*—Louise N. Leary
*Attorney, Agent, or Firm*—Sterne, Kessler, Goldstein & Fox P.L.L.C.

[57] ABSTRACT

The invention concerns novel 6- or 7-substituted derivatives of esculetin (6,7-dihydroxy-2H-1-benzopyran-2-one), their synthesis, and their application as substrates for the detection of micro-organisms in samples where a derivative is enzymatically cleaved to release a colored or fluorogenic marker which has a low tendency to diffuse through agar or other aqueous environments.

19 Claims, No Drawings

ESCULETIN DERIVATIVES

CROSS REFERENCE TO RELATED APPLICATIONS

This application claims priority to International Application No. PCT/GB97/01202, filed May 1, 1997.

FIELD OF THE INVENTION

The present invention relates to novel esculetin derivatives and their application as substrates for the specific detection of micro-organisms.

BACKGROUND OF THE INVENTION

Esculetin is the aglycone of esculin and of cichoriin and can obtained by hydrolysis of these molecules. Esculetin has the following chemical formula:

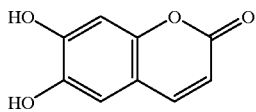

The full chemical name of esculetin is 6,7-dihydroxy-2H-1-benzopyran-2-one (also known as 6,7-dihydroxycoumarin or cichorigenin).

The presence of β-D-glucosidase has long been regarded as an important diagnostic marker in microbial identification. The most commonly used substrate for the detection of this enzyme is the naturally occurring glycoside esculin (6,7-dihydroxycoumarin-6-glucoside or 6-(β-D-glucopyranosyloxy)-7-hydroxy-2H-1-benzopyran-2-one).

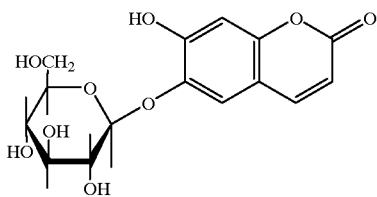

Hydrolysis of esculin yields β-D-glucose and esculetin (6,7-dihydroxycoumarin), the latter compound being detected by the formation of a brown/black complex in the presence of iron salts. This test was first applied in the identification of enterococci and has since found wide application in the identification of other genera (Swan, A. J. *Clinical Pathology* 7 160–163 (1954), Trepeta et al *Antonie van Leewenhoek* 53 273–277 (1987)). The main disadvantage of this substrate is that, when incorporated into agar, the resulting complex formed spreads throughout the medium (James et al *Zbl. Bakt. Hyg.* A267 188–193 (1987)). This creates difficulties in distinguishing β-glucosidase producing colonies when present within a mixed culture.

Synthetic substrates are also available for detection of β-D-glucosidase to yield either chromogenic or fluorescent compounds upon hydrolysis (Manafi et al *Microbiol. Reviews* 55 335–348 (1991)). For example, the fluorogenic compound 4-methylumbelliferyl-β-D-glucoside has been widely used although it has several disadvantages when incorporated into an agar medium. These include the fact that the recognition of colonies can only be performed under the presence of long wave ultraviolet light and also the glucose released from the substrate by hydrolysis, may be utilised by the organisms to produce acid. This causes a reduction in the fluorescence produced by 4-methylumbelliferone due to the predominance of the undissociated form of the molecule at low pH. In addition, the released umbelliferone has a tendency to diffuse through the agar, creating difficulties distinguishing individual colonies producing the target enzyme. Other substrates commonly employed include β-D-glucoside derivatives of nitrophenol (Trepeta et al *Antonie van Leewenhoek* 53 273–277 (1987)). However, widespread diffusion is again a severely limiting factor when incorporating such substrates into solid media (Manafi et al *Microbiol. Reviews* 55 335–348 (1991)).

β-galactosidase is also an important diagnostic marker in microbial identification. It is perhaps the most widely studied of all microbial enzymes and its presence has long been recognised as a valuable taxonomic marker. This is particularly true in the bacterial family Enterobacteriaceae where assay of β-galactosidase has been used for many years for the differentiation of non-lactose fermenting species from slow or late lactose fermenters (James, A. L., In *Chemical Methods in Prokaryotic Systematics*, 471–492, ed. Goodfellow and O'Donnell, Wiley & Sons (1994)). Numerous substrates are available for the detection of β-galactosidase, the most common being ortho-nitrophenyl β-D-galactoside (ONPG) which releases yellow o-nitrophenol upon hydrolysis (Lowe, G. H., *J. Medical Laboratory Technology* 19 21 (1962)). Fluorogenic substrates have also been used utilising labels such as resorufin, fluorescein and 4-methylumbelliferone (Manafi et al *Microbiol. Reviews* 55 335–348 (1991), Plovins et al *Applied and Environmental Microbiol.* 60 4638–4641 (1994)).

An important application of the β-galactosidase assay is the detection of "coliforms" in water and food samples. This has led to the development of membrane filtration techniques which incorporate a suitable substrate for the direct detection of β-galactosidase (Brenner et al *Applied and Environmental Microbiol.* 59 3534–3544 (1993), Ceneci et al *Microbios* 76 47–54 (19)). The most widely used substrate for this purpose is 4-methylumbelliferone β-D-galactoside. For example, this substrate was used in a rapid assay which allowed detection of as few as 1 faecal coliform per 100 ml in six hours (Berg et al *Applied and Environmental Microbiol.* 54 2118–2122 (1988)). The limitations of this substrate are that the released 4-methylumbelliferone readily diffuses across the filter and the fluorescence produced can only be visualised under ultra-violet light.

Due to the limitations of these substrates for identification of β-glucosidase and β-galactosidase, chromogenic compounds have been employed which yield insoluble products upon hydrolysis. Such substrates provide the advantage that the released chromogen remains localised around the bacterial colony without diffusing through the medium (Kodaka et al *J. Clinical Microbiol.* 33 199–201 (1995)). Examples of these for the detection of β-glucosidase include, indoxyl β-D-glucoside and 5-bromo-4-chloro-3-indolyl β-D-glucoside and examples for the detection of β-galactosidase include galactosides of indoxyl and its halogenated derivatives such as 5-bromo-4-chloro-3-indolyl β-D-galactoside (X-gal) (Kodaka et al *J. Clinical Microbiol.* 33 199–201 (1995)). The aglycone released by hydrolysis from these substrates is rapidly oxidised by air to form a purple/blue indigoid dye on the colony mass (James, A. L., In *Chemical Methods in Prokaryotic Systematics*, 471–492, ed. Goodfellow and O'Donnell, Wiley & Sons (1994)). Whilst these substrates are highly effective, they are relatively difficult to prepare and although commercially available, their extremely high cost has proved prohibitive for large scale diagnostic use. The use of 8-hydroxyquinoline β-D-glucoside has also been described as an alternative to esculin for the detection of β-glucosidase (James et al *Zbl. Bakt. Hyg.* A267 188–193 (1987)). Although impressive results were obtained, toxicity problems have been encountered particularly with Gram positive organisms (Albert et al *British Journal of Experimental Pathology* 34 119–130 (1953)).

SUMMARY OF THE INVENTION

The present invention relates to certain novel 6- or 7-substituted derivatives of esculetin (6,7-dihydroxycoumarin) which are microbially hydrolysable to fluorescent, iron-chelating esculetin moieties which have a low tendency to diffuse through agar or other aqueous environments without suffering from all the disadvantages referred to above.

DESCRIPTION OF THE PREFERRED EMBODIMENTS

According to a first aspect of the present invention there is provided a compound of general formula I:

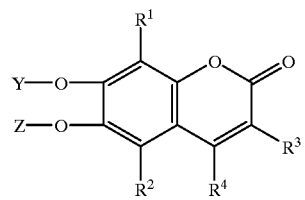

(I)

wherein each of $R^1$ and $R^2$ independently represents a hydrogen or a halogen atom or another group which does not interfere with subsequent iron chelation;

each of $R^3$ and $R^4$ independently represents a hydrogen atom or a ($C_1$–$C_8$)alkyl or ($C_6$ or $C_{10}$)aryl($C_1$–$C_8$)alkyl or an optionally modified carboxyl-bearing group of the general formula —$CH_2(CH_2)_n COX$, where n is a number from 0 to 3 and X represents a hydroxyl group or another hydrophillic group, and, $R^3$ may alternatively represent an acyl group of the general formula —COR, in which R represent a ($C_1$–$C_8$) alkyl, ($C_6$ or $C_{10}$)aryl($C_1$–$C_8$)alkyl or ($C_5$–$C_8$)cycloalkyl group, provided that $R^3$ and $R^4$ between them contain at least three carbon atoms;

or $R^3$ and $R^4$ together with the carbon atoms to which they are attached form a ($C_5$–$C_8$)cycloalkene ring; and one of Y and Z represents an enzymatically cleavable group and the other of Y and Z represents a hydrogen atom; or a suitable salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

The expression "atom or group which does not interfere with iron chelation" refers to the fact that one of the principle means of detection if aglycones of general formula I is by chelation by means of hydroxyl groups at the 6 and 7 positions of the coumarin ring system. Groups which do not interfere with this chelation may be substituted at $R^1$ and/or $R^2$. Examples include hydrogen, hydroxyl, halogen or ($C_1$–$C_6$)alkyl. The halogen atom may be a fluorine atom or a chlorine atom and the lower alkyl group may be methyl, ethyl, propyl, butyl or benzyl.

As used herein the term "($C_1$–$C_8$)alkyl" refers to straight chain or branched chain hydrocarbon groups having from one to eight carbon atoms. Illustrative of such alkyl groups are methyl, ethyl, propyl, isopropyl, butyl, isobutyl, sec-butyl, tert-butyl, pentyl, neopentyl, hexyl, heptyl and octyl. From one to four carbon atoms may be preferred.

As used herein the term "($C_1$–$C_{10}$)alkyl" refers to straight chain or branched chain hydrocarbon groups having from one to ten carbon atoms. Illustrative of such alkyl groups are methyl, ethyl, propyl, isopropyl, butyl, isobutyl, sec-butyl, tert-butyl, pentyl, neopentyl, hexyl, heptyl, octyl, nonyl and decyl. From one to six carbon atoms may be preferred.

The term "($C_6$ or $C_{10}$)aryl" includes phenyl and naphthyl.

As used herein, the term "($C_5$–$C_8$)cycloalkyl" refers to an alicyclic group having from 5 to 8 carbon atoms. Illustrative of such cycloalkyl groups are cyclopentyl and cyclohexyl.

As used herein, the term "($C_5$–$C_8$) cycloalkene ring" refers to an alicyclic ring having from 5 to 8 atoms and having in addition one or more double bonds. Illustrative of such cycloalkenyl groups are cyclopentenyl, cyclohexenyl, cycloheptenyl and cyclooctenyl.

In compounds of this invention, the presence of an asymmetric carbon atom gives rise to enantiomers. The presence of several asymmetric carbon atoms give rise to diastereoisomers, each of which consists of two enantiomers, with the appropriate R or S stereochemistry at each chiral centre. The invention is understood to include all such diastereoisomers, optically active enantiomers and mixtures thereof.

The term "suitable salt" refers to a salt prepared by contacting a compound of formula I with an acid or base whose counterpart ion does not interfere with the intended use of the compound. Examples include the sodium salt or magnesium salt of a phosphate derivative or the salt formed from a primary, secondary or tertiary amine where the compound of general formula I is a carboxylic acid. An example of a primary amine salt can be the cyclohexylammonium salt, a suitable secondary amine salt may be the piperidine salt and a tertiary amine salt may be the triethylamine salt.

Preferred compounds of general formula I include those in which, independently or in any compatible combination:

$R^1$ is chlorine or, preferably hydrogen;

$R^2$ is chlorine or, preferably hydrogen;

$R^3$ is ($C_1$–$C_4$)alkyl, particularly butyl, or benzyl;

$R^4$ is ($C_1$–$C_4$)alkyl; or, —$CH_2(CH_2)_n COX$, where n is a number from 0 to 3 and X represents a hydroxyl group or one of the following hydrophillic groups, namely:

—NHCH$_2$CONHCH$_2$CO$_2$H

—NHCH$_2$CONHCH$_2$CONHCH$_2$CO$_2$H

—NHCHCH$_2$CONH$_2$
     |
     CO$_2$H

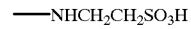

—NHCH$_2$CH$_2$SO$_3$H

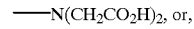

—N(CH$_2$CO$_2$H)$_2$, or,

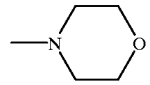

$R^3$ and $R^4$ together with the carbon atoms to which they are attached form a ($C_5$–$C_8$)cycloalkene ring, preferably a cyclopentenyl or cyclohexenyl ring;

where $R^3$ is —$CH_2(CH_2)_n COX$, where n is a number from 0 to 3, then the group X is as previously defined, the enzymatically cleavable group represented by Y or Z is an α- or, preferably, β-linked sugar residue such as β-D-glucose, β-D-galactose, β-D-xylose, β-D-glucuronic acid or N-acetyl-β-D-glucosamine, or a phosphate or a carboxylate ($R^5 COO$—) group, where $R^5$ represents a ($C_1$–$C_{10}$)alkyl group. Sugar residues, particularly those derived from glucose and galactose, are the most preferred compounds.

Compounds in which $R^3$ and $R^4$ together with the carbon atoms to which they are attached form a cyclopentene or a cyclohexene ring are especially preferred.

The aglycone moiety of general formula I is a substituted esculetin. When Y is a glucose moiety and Z is hydrogen (i.e. when the esculetin ring system is substituted at the 7-position) the compounds of general formula I are cichoriins. When Y is a hydrogen atom and Z is a glucose moiety (i.e. when the esculetin ring system is substituted at the 6-position) the compounds of general formula I are esculins. Cichoriins, and analogues of cichoriins when the sugar residues other than glucose are substituted at the 7-hydroxyl group position, are preferred. This is because the fluorescent capabilities of the esculetin ring system are quenched by the presence of the sugar substituent at the 7-position; therefore hydrolysis of the fluorogenic, as opposed to fluorescent, cichoriin (or other sugar analogue) to release the esculetin can be observed by an increase in fluorescence. Since esculins (and other sugar analogues) already have no 7-hydroxy substituent, they fluoresce even in the conjugated state, so no differentiation form the free aglycone can be observed by fluorescence alone.

Where the compound of general formula I is an organic ester, each of Y or Z may independently represent an ($C_1$–$C_{10}$)alkylcarbonyl group. Preferred esters include the octanoate and butyrate esters. Ester derivatives are useful where the microbial enzyme is an esterase.

Preferred compounds of general formula I are:

3,4-cyclohexenoesculetin-β-D-galactoside,

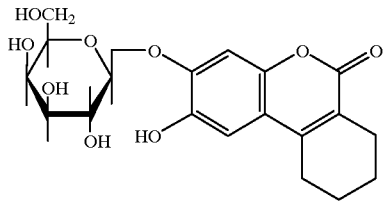

3,4-cyclohexenoesculetin-β-D-glucoside,

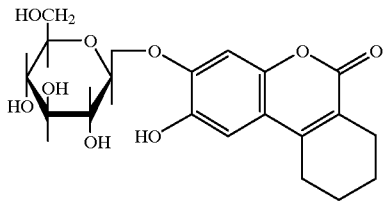

3,4-cyclohexenoesculetin-β-D-glucuronide,

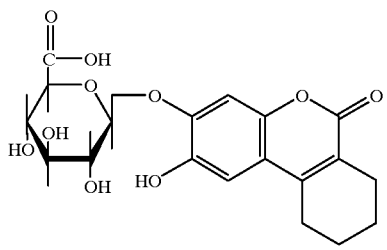

3-benzyl-4-methylesculetin-β-D-glucoside,

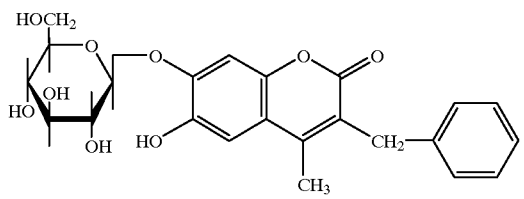

3,4-cyclohexenoesculetin-N-acetyl-β-glucosaminide,

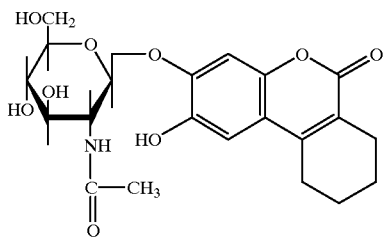

3,4-cyclohexenoesculetin-β-D-xyloside

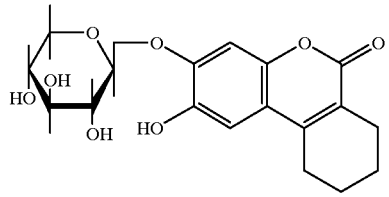

3-n-butyl-4-methylesculetin-β-D-galactoside,

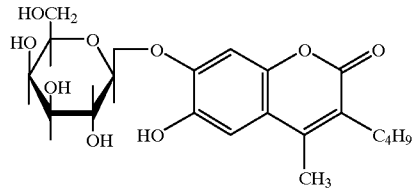

3-n-butyl-4-methylesculetin-β-D-glucoside,

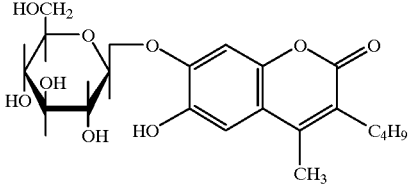

-continued

N(-7(6)-octanoyloxy-6(7)-hydroxycoumarin-4-acetyl) glycylglycine,

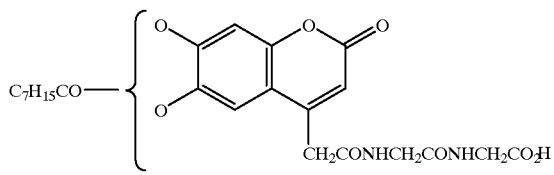

N(-7(6)-butyryloxy-6(7)-hydroxycoumarin-4-acetyl) glycylglycine,

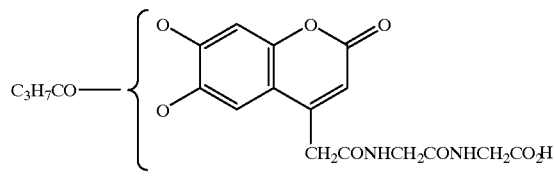

3,4-cyclohexenoesculetin-6(7)-phosphoric acid.

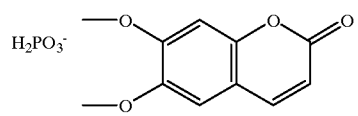

cyclohexylammonium 3-acetate-6-hydroxy-7-octanoyl coumarin,

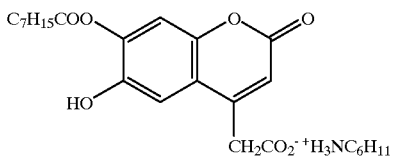

According to a second aspect of the present invention, there is provided a process for the preparation of the compounds defined in general formula I, comprising derivatising an optionally protected compound of general formula II at position 6 or 7, and optionally thereafter converting the compound of general formula I so formed into another compound of general formula I.

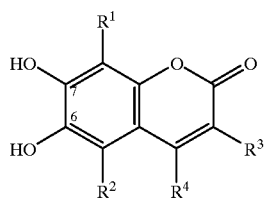

Derivatising the compound of general formula II to form a compound of general formula I, includes glycosylation, phosphorylation and esterification.

The glycoside derivative of the compounds of general formula II may be formed by treating the compound with a glycoside under suitable conditions. Glycosylation of an esculetin derivative occurs at the 7-position on the coumarin ring unless this position is blocked in which case glycosylation may take place at the 6-position. An example of a suitable blocking group is a benzylic halide, such as benzyl chloride, benzyl bromide, benzyl iodide, or other group such as benzyl cyanide (Greene *Protective Groups in Organic Synthesis,* publ. Wiley-Interscience 97–99 (1981)). Glycosylation is then followed by debenzylation by suitable treatment.

It is preferred that the hydroxyl groups of the glycoside be protected by addition of a removable protector group such as an acetyl moiety. An example of a suitable protected glycoside compound is the tetraacetyl form of the β-glucoside or β-galactoside. The tetraacetyl derivative may be derived from the corresponding α-acetobromohexose. Deprotection of the hydroxyl groups may be undertaken at any particular time, but in practice this will be the final step in the formation of the desired compound. Deprotection may comprise treatment with a solution of sodium methoxide in methanol where the protector group is an acetyl moiety. Conditions for glycosylation may be chosen by the person skilled in the art without undue experimentation. However, suitable conditions may comprise treating the protected glycoside of the esculetin in a solution of potassium hydroxide in aqueous acetone, followed by deprotection.

Organic esters may be formed from the appropriate 6,7-dihydroxycoumarin carboxylic acid of general formula II. The dihydroxycoumarin carboxylic acid may be optionally first acetylated to protect the 6- and 7-hydroxyl groups and can then converted to the acid chloride by addition of thionyl chloride. The mono-, di-, or tri-aminoacyl can be formed by conjugation of the acid chloride with the appropriate aminoacyl compound. The aminoacyl conjugate may be esterified by treatment with a $(C_1-C_{10})$alkyl carbonylhalide in the presence of pyridine. Examples of suitable alkyl carbonylhalides include, octanoyl chloride or butyryl chloride.

Formation of phosphate ester derivatives may be achieved by treating the esculetin derivative with phosphorous chloride ($POCl_3$) in the presence of pyridine (or other appropriate monophosphorylating agent).

As mentioned above a compound of general formula I can optionally be modified to another compound of general formula I. For example, where either Y or Z represent an enzymically cleavable group, such as a glycoside residue, the glycoside may be modified in situ; e.g. a glucose residue may be modified to a glucuronic acid residue with oxygen in the presence of platinum catalyst and carbon. Similarly other glycosides may be oxidised to their 6-carboxyl derivatives (glycuronic acids). In addition, 7-substituted substrates e.g. β-glucosides of general formula I where Y is glucose, can by appropriate reactions at the vacant phenolic group (6-hydroxyl) yield other substrates e.g. carboxyl esters, followed by deprotection of the 7-substituent with Sweet Almond β-glucosidase. This yields derivatives of the esculinic series.

The compounds of general formula II may be prepared by treating an appropriate linear or cyclic β-ketoester (substituted or unsubstituted) of general formula III with a compound of general formula IV in a Pechmann condensation.

The β-ketoesters of general formula III are as follows:

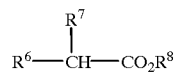

wherein,
each of $R^6$ and $R^7$ independently represent an acetyl ($CH_3CO$—) or an acyl group of the formula $X(CH_2)_nCO$—, where n is a number from 0 to 6 and X represents:
(i) hydrogen, $(C_1-C_8)$alkyl, $(C_5-C_8)$cycloalkyl or $(C_6$ or $C_{10})$aryl$(C_1-C_8)$alkyl,
(ii) —$CO_2CH_3$ or —$CO_2C_2H_5$, or
(iii) $C_2H_5OOCCH_2CO$—, where n is 1;
or, R⁷ represents hydrogen, a (C₁–C₈)alkyl, (C₅–C₈) cycloalkyl, a (C₆ or C₁₀)aryl(C₁–C₈)alkyl, or a (C₆ or C₁₀)aryl(C₁–C₈)alkyl aroyl group;

or,

R⁶ and R⁷ together form a cyclic ketone —(CH₂)ₙCO—, where n is a number between 4 and 7;

and,

R⁸ represents (C₁–C₈)alkyl, phenyl or methylphenyl.

Of the β-ketoesters of general formula III, where R⁶ and R⁷ form a cyclic ketone, cyclopentanone and cyclohexanone are preferred. It is also preferred that R⁸ is butyl or methylphenyl.

The compounds of general formula IV are:

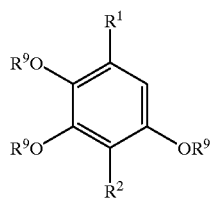

(IV)

wherein, each R⁹ independently represents hydrogen or (C₁–C₈) alkyl-CO;

R¹ and R² are as described previously.

The preferred compounds of general formula IV are 1,2,4-trihydroxybenzene derivatives

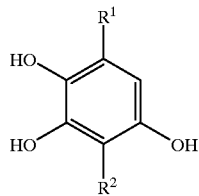

where R¹ and R² are as described previously.

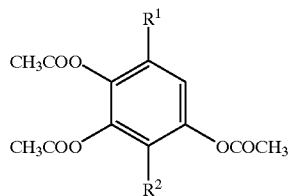

In practice, however, 1,2,4-trihydroxybenzene is relatively unstable and the preferred starting material is therefore 1,2,4-triacetohydroxybenzene. 1,2,4-triacetohydroxybenzene may be synthesised by Thiele-Winter acetylation of the corresponding benzoquinone compound.

Preferred β-ketoesters are:

ethyl-2-n-butylacetoacetate ethyl-2-benzylacetoacetate, ethyl-2-cyclohexanone carboxylate, and ethyl-2-cyclopentanone carboxylate.

The product of this step is a compound of general formula II as defined above. Other compounds mentioned are trivially synthesisable by methods known in the art.

The formation of 6,7-dihydroxycoumarin carboxylic acids within general formula II may be carried out by treating a suitable β-ketoester of general formula III, where X is (a) —CO₂CH₃, or —CO₂C₂H₅ where n is a number between 0 and 6, or (b) C₂H₅OOCCH₂CO—, where n is 1, with a compound of general formula IV as defined above.

Preferred starting compounds include diethylacetone dicarboxylate, dimethyl 2-acetylglutarate or diethyl acetylglutarate. Where diethylacetone dicarboxylate is treated with 1,2,4-triacetoxybenzene, the product is 6,7-dihydroxycoumarin-4-acetic acid, after hydrolysis.

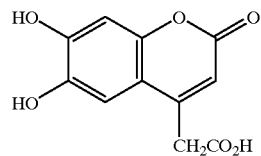

Starting materials not already described are trivially synthesisable by methods known in the art.

According to a third aspect of the present invention, there is provided a composition comprising a compound of general formula I and optionally a microbiologically acceptable diluent, excipient or substrate. The substrate may be a solid or semi-solid growth support medium or a liquid growth support medium.

Agar is the traditional support medium used in microbiology for the growth of microorganisms. It is prepared by autoclaving the dehydrated agar in water with other components as necessary. The autoclaving process at temperatures above 100° C. causes the agar to rehydrate to form a gelatinous liquid agar solution. The liquid agar formed is allowed to cool slightly and is then poured, while still liquid, into suitable containers such as culture plates or Petri dishes. The agar will gel to form a support medium upon further cooling. The choice of agar will depend on the strain of micro-organism to be grown but may be selected from the one of the following preparations: bacteriological agar, Columbia agar, noble agar, select agar, brain-heart infusion agar, LB agar or Lennox Broth agar, luria agar, yeast extract or tryptone digest. Other choices of medium are described in Sambrook et al *Molecular Cloning,* 2nd edition, A1–A3, Cold Spring Harbor Laboratory (1989) and in *Difco Manual* 10th edition, Difco Laboratories, Detroit, Mich., USA.

The compounds of the present invention may admixed with the dehydrated agar as separate components or prepared as combined particles as appropriate.

Typically, the growth medium selected may also comprise one or more essential nutrient, mineral, vitamin and/or antibiotic to select, promote or assist the growth of a particular micro-organism or to assist in the identification or enumeration of a particular micro-organism. Antibiotics commonly used in micro-biological growth media include: ampicillin, chloramphenicol, D-cycloserine, gentamicin, kanamycin, nalidixic acid, rifampicin, spectinomycin, streptomycin and tetracycline. Essential nutrients include amino acids for which the micro-organism to be grown is growth deficient or a fermentable carbon source such as a carbohydrate. It may also be necessary to add certain minerals, such as for example magnesium, calcium, sodium, potassium or iron, in the form of an appropriate salt, or ammonium or phosphate salts.

The growth of micro-organisms on a solid support medium such as agar can be carried out in a suitable container and in practice this will be the Petri dish or culture plate. Typically the container comprises a base with an overhanging lid to permit oxygen to be supplied to aerobic bacteria when the plate is being incubated. Where anaerobic bacteria are being cultured then the lid may be sealed to the base or the plate may be incubated in an anaerobic incubator.

According to a fourth aspect of the present invention there is provided a method for the detection and/or identification of micro-organisms in a sample, comprising the step of (a) growing a micro-organism isolated from the sample on a growth support medium containing a compound of general formula I and detecting the release of an identifiable chromogenic or fluorogenic marker following hydrolysis of the compound of general formula I. The microorganisms may also be present in a liquid growth support medium or a liquid sample to be analysed.

The method according to the present invention can be used to detect both Gram negative and Gram positive bacteria. The method has application to, but is not limited to, the detection of the following genera: Enterococcus, Listeria, Streptococcus, Citrobacter, Enterobacter, Escherichia, Hafnia, Klebsiella, Proteus, Providencia, Salmonella, Serratia, Shigella and Yersinia.

The fluorescent or, in conjunction with iron, coloured marker detected in the method is the result of the hydrolysis of the compound of general formula I which liberates the esculetin moiety. Hydrolysis of the compound may be characteristic of the presence of a micro-organism to be detected.

Specific detection of micro-organisms is required in hospitals to assist in clinical diagnosis and effective assessment of an appropriate course of medical treatment. Common biological samples that a clinician will want analyse for their micro-organism content are saliva, urine, blood, faeces, the contents of the stomach or a biopsy sample. The food and drinks industries also require specific detection of micro-organisms in order to monitor and maintain product quality and safety. Similarly, the water industry also needs to be able to monitor the presence and quantity of micro-organisms present in the water supply. Suitable samples for analysis in the method according to this aspect of the invention will therefore be an edible substance, water or other potable liquid.

The method in its preferred form utilises the various novel esculetin derivatives as indicators of particular enzymatic activities by incorporation into agar media. Because of the essentially non-spreading character of the iron chelate produced, colonies can be visualised and, provided that the media are appropriately selective, identified. The method adapts well to the use of cellulose nitrate membrane filters and thereby to colony counting.

The compounds of the present invention may be present in the growth support medium at an effective concentration which may be of from 0.1 mg/ml to 2 mg/ml, suitably of from 0.2 mg/ml to 1 mg/ml and preferably of from 0.4 mg/ml to 0.8 mg/ml. It is preferred that a concentration of 0.5 mg/ml be used when the growth support medium is Columbia agar.

Accordingly, the present invention also extends to a kit comprising a growth medium containing a compound of general formula I. The kit may additionally comprise a container such as a Petri or culture dish.

Preferred features for the second and subsequent features of the invention are as for the first aspect mutatis mutandis.

EXAMPLES

The invention will now be described by way of example with reference to the accompanying Examples which are provided for the purposes of illustration and are not to be construed as being limiting on the present invention.

Examples 1 to 4

Synthesis of Substituted Esculetins (6,7-dihydroxycoumarins)

Materials

Columbia agar was obtained from Lab M, Bury, UK. Chemicals involved in the synthesis of the esculetin derivatives were all obtained from the Aldrich Chemical Company Ltd, Gillingham, UK.

Example 1

Synthesis of 6,7-dihydroxy-3 4-cyclohexenocoumarin

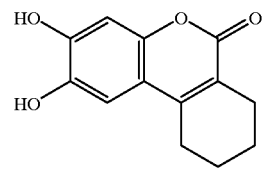

1,2,4-triacetoxybenzene (6.3 g, 25 mmol) and ethyl cyclohexanone-2-carboxylate (4.25 g, 25 mmol) with heated together in a small flask until a homogenous viscous liquid was obtained. The lowest temperature possible was employed. The hot liquid was cooled somewhat and a magnetic stirrer introduced. Cooling below 30° C. caused solidification and therefore at this temperature 75% w/w sulphuric acid (35 ml) cooled to 10° C. was rapidly added to the stirred liquid. This lowered the temperature whilst maintaining homogeneity. The reaction was allowed to continue at ambient temperature for 6 hours, a white suspension forming after about 3 hours.

The suspension was poured in a thin stream into rapidly stirred ice/water (300 ml) and gave a suspension of cream-coloured solid. After stirring for 10 minutes, the solid was removed by vacuum filtration, washed with abundant water, and sucked dry, then air dried at 40–50° C. The crude material was crystallised from hot ethanol. On cooling, pale yellow needles separated. These were removed by vacuum filtration and air dried (5.2 g (89%)).

Example 2

Synthesis of 6,7-dihydroxy-3-benzyl-4-methyl Coumarin 1,2,4-triacetoxybenzene (6.3 g, 25 mmol) and ethyl 2-benzylacetoacetate (5.5 g, 25 mmol) were heated together as described in Example 1. 75% sulphuric acid (35 ml) was added to the stirred solution and stirring continued for 16 hours. The dark coloured suspension was poured into ice/water (350 ml) with good stirring and the grey suspension filtered and the residue washed with abundant water. The residual solid was air dried and recrystallised from hot ethanol with subsequent addition of a little water to aid crystallisation. The esculetin derivative formed small white needles (5.5 g, 75.3%).

Example 3

Synthesis of 6,7-dihydroxy-3-acetyl-4-methylcoumarin

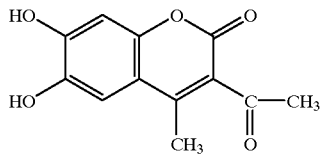

1,2,4-triacetoxybenzene (6.3 g, 25 mmol) and ethyl diacetoacetate (4.3 g, 25 mmol) were heated together as described previously and treated with 75% sulphuric acid (35 ml). After 16 hours the crude product was isolated by pouring into ice/water. The air dried material was crystallised from hot ethanol with addition of hot water to the point of crystallisation. On cooling, pale yellow needles formed (3.5 g, 60%).

Example 4

Synthesis of 6,7-dihydroxy-4-methyl coumarin-3-propionic Acid

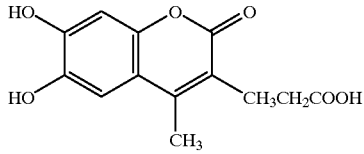

1,2,4-triacetoxybenzene (6.3 g, 25 mmol) and dimethyl 2-acetylglutarate (5.75 g, 25 mmol) were heated together and treated with 75% sulphuric acid (35 ml) as described previously. After stirring for 20 hours, the crude material was isolated by pouring into ice/water and the product collected after washing with water. The product (ethyl 6,7-dihydroxy-4-methyl coumarin 3-propionate) was crystallised from hot ethanol (4.1 g, 56%).

The ester was hydrolysed by stirring with an aqueous solution of potassium hydroxide (3% w/v) comprising water (90 ml) and ethanol (10 ml). After several hours, a test sample revealed no residual ester (TLC using ethyl acetate-:Toluene (3:1)—u.v. inspection). The alkaline solution was stirred and acidified to pH 2–3 using hydrochloric acid (2 M). The precipitated acid was removed by vacuum filtration, washed with water and recrystallised from hot methanol/water mixture (1:1) (2.95 g, 44.6%).

Cognate Preparation: 6,7-dihydroxycoumarin-4-acetic Acid

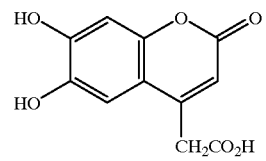

This was prepared as in example 4 by substitution of diethyl acetone dicarboxylate (5.05 g, 25 mmol) for the ester employed. The temperature of the 20 hour reaction was kept at 10–15° C. to prevent possible hydrolysis and decarboxylation. The isolated acid amounted to 2.4 g (47%).

The triacetoxybenzene employed in the above synthetic procedures was either purchased (Lancaster Synthesis Ltd, Morecambe, Lancs) or made by Thiele-Winter acetylation of p-benzoquinone using acetic anhydride.

Examples 5 to 10

Synthesis of Glycosides and Related Compounds

Example 5

Synthesis of 3,4-cyclohexenoesculetin-β-D-glucopyranoside

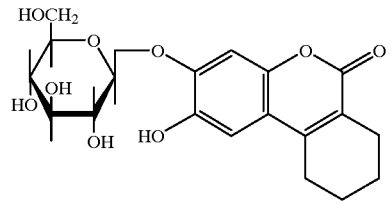

3,4-cyclohexenoesculetin (6,7-dihydroxy-3,4-cyclohesenocoumarin) (3.5 g, 15 mmol) was dissolved in an aqueous solution of potassium hydroxide; 16 ml of 10% w/v KOH (29 mmol). With stirring, the esculetin rapidly dissolved. To this was added α-acetobromoglucose (6.25 g, 15 mmol) dissolved in acetone (18 ml). The solution was homogenous and became lighter in colour on stirring. After 18 hours at 10–15° C. a yellow precipitate formed. This was removed by filtration to give a yellow cake (3.0 g dryweight).

The filtrate was poured slowly into stirred ice-water (200 ml). The precipitate which formed was filtered onto a Buchner funnel, washed with water and dried to give a gummy mass. This was dissolved in dichloromethane (50 ml) with warming. The slight precipitate which formed on cooling was removed. TLC showed this to be 3,4-cyclohexenoesculetin. The filtrate contained the tetraacetyl glycoside with a trace of the esculetin.

The yellow cake was powdered and extracted with hot dichloromethane and the suspension filtered the residue (1.4 g) of the esculetin was retained for future glycosidation. The filtrate from this was combined with the previous dichloromethane extract, dried with magnesium sulphate (anhydrous) and rotary evaporated to give a pale solid. This was dissolved in hot methanol and recrystallised therefrom to give small colourless crystals of the pure tetraacetyl compound (2.5 g, 29%).

Deacetylation was effected using sodium methoxide in methanol. Freshly cut sodium 1.0 g was dissolved in methanol (100 ml).

The tetraacetyl compound (2.5 g) was dissolved in methanol (50 ml) and treated with sodium methoxide solution (20 ml) the progress of deacetylation was followed by TLC until only baseline material (solvent—ethyl acetate/toluene, 3:1) remained. The methanolic solution was brought to pH 6.5 by addition of aliquots of Amberlite 1R120($H^+$), analytical grade, washed after treatment with acid. The supernatant liquid was decanted from the resin and the latter washed with methanol (3×10 ml). Methanol was removed by rotary evaporation at 30–40° C. and the residual solid crystallised from methanol/water (1.5 g, 86%).

Example 6

Synthesis of 3-benzyl-4-methyl esculetin-β-D-glucopyranoside

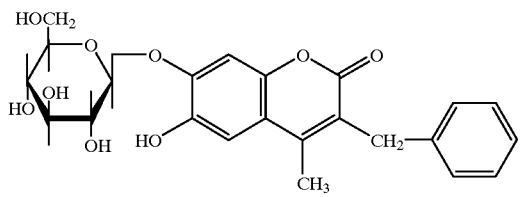

3-benzyl-4-methyl esculetin (Example 2) (4.25 g, 15.6 mmol) was dissolved in an aqueous solution of potassium hydroxide (16.5 ml of 10% w/v KOH (29 mmol) with stirring.

A yellow solid, the potassium salt, soon separated. A solution of α-acetobromoglucose (6.6 g, 16 mmol) dissolved in acetone (20 ml) was added to the stirred solution. Further addition of acetone (3–4 ml) ensured homogeneity. The light brown solution was stirred overnight (16 hours). The resulting paste was filtered with suction and the residue sucked dry, then air dried at room temperature. The tetraacetylglucoside was extracted into hot chloroform (3×30 ml) and the resulting suspension filtered from a scanty precipitate. The chloroform solution was washed with cold dilute (3%) sodium carbonate solution (3×30 ml) followed by water. The organic phase was dried using anhydrous magnesium sulphate and rotary evaporated yielding a white solid. This was dissolved in hot ethanol (100 ml) and cooled to 0° C. overnight. The crystals were removed by suction filtration and pressing. After drying in a vacuum over the product weighed 3.0 g(32%). Deacetylation of the tetraacetylglucoside (3.0 g) using methanolic sodium methoxide was achieved as described in Example 5, and gave the β-glucoside (1.8 g, 81.4%).

Example 7

Synthesis of 3,4-cyclohexenoesculetin-β-D-galactopyranoside

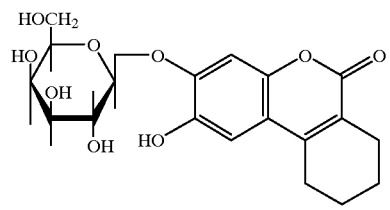

3,4-cyclohexenoesculetin (6.95 g, 30 mmol) was dissolved in an aqueous solution of potassium hydroxide (35 ml of 10% w/v KOH (62.5 mmol). α-acetobromogalactose (13.6 g, 33 mmol) was dissolved in acetone (36 ml) and this solution was added to the stirred aqueous esculetin solution. Addition of a little more acetone was needed to give a homogenous solution. The reaction mixture was stirred overnight (10–15° C.). Precipitation commenced after 4 hours. The suspension was filtered after 16 hours. The residue <1 g was shown to be mainly the unchanged esculetin, and was rejected. The filtrate was biphasic, consisting of a lower viscous phase and an upper aqueous layer. The lower phase, after separation was poured slowly into well stirred ice/water (250 ml) to give an abundant white precipitate. This was removed by suction filtration, washed with cold water and dried. The dry solid was dissolved in dichloromethane. TLC showed a large fast-running spot of the tetraacetyl galactoside and very little of the esculetin.

The aqueous upper layer from the reaction mixture was concentrated by rotary evaporation at 30–40° C. and poured into ice water. The product was much less than from the lower layer but still contained a substantial amount of the desired product. The precipitated solid was removed by suction filtration, dried and dissolved in dichloromethane.

The combined dichloromethane solutions were washed with dilute aqueous sodium carbonate (2×50 ml) and then with water. After drying with anhydrous magnesium sulphate, the solvent was removed by rotary evaporation at 30° C. to give a viscous oil which did not solidify.

The oily tetraacetyl galactoside was deprotected by solution in methanol and addition of methanolic sodium methoxide (30 ml of 1% solution) as described in Example 5. After evaporation of methanol, the galactoside formed an oil which rapidly solidified to a mass of white crystals (5.2 g, 44.8%)

Example 8

Synthesis of 3,4-cyclohexeno Esculetin-β-D-glucuronide

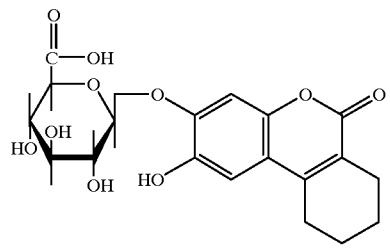

To a stirred solution of 3,4-cyclohexenoesculetin (2.32 g, 10 mmol) and methyl 2,3,4-tri-O-acetyl glucopyranosyl bromide uronate (3.97 g, 10 mmol) in freshly distilled quinoline (20 ml), was added freshly prepared silver (I) oxide (1.86 g, 15 mmol). The mixture was stirred at ambient temperature for 24 hours in absence of light. The resulting slurry was filtered with suction, the residue being washed with cold acetone until light grey in colour. The filter was added slowly to stirred cold hydrochloric acid (200 ml, 2 M) yielding a dense grey precipitate which was collected by suction filtration and washed with more 2 M hydrochloric acid (2×30 ml) the residue was sucked dry and dried in a vacuum drying oven at ambient temperature. Recrystallisation from methanol gave an off-white solid (0.82 g, 15%).

The acetylated methyl uronate was deprotected by solution in methanol and addition of one-fifth mol. ratio of methanolic sodium hydroxide (95% methanol/5% water). After stirring for 5 hours, methanol was removed by rotary evaporation. Water (10 ml) was added and the solution neutralised with 2 M hydrochloric acid. Water was removed by rotary evaporation at 60° C. and the residue suspended and stirred in acetone for 1 hour. The suspended glucuronide was removed by suction filtration and acetone removed by rotary evaporation to give an amorphous light brown powder (0.41 g, 65%).

3,4-cyclohexenoesculetin-β-D-xylopyranoside and 3,4-cyclohexenoesculetin-N-acetyl-β-D-glucosaminide By similar procedures to those described, the following glycosides were synthesised although not isolated in a pure state.

3,4-cyclohexenoesculetin-β-D-xylopyranoside

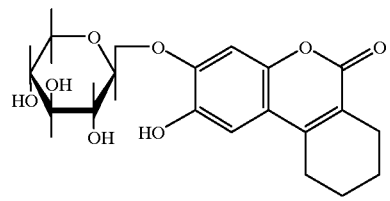

3,4-cyclohexenoesculetin-N-acetyl-β-D-glucosaminide

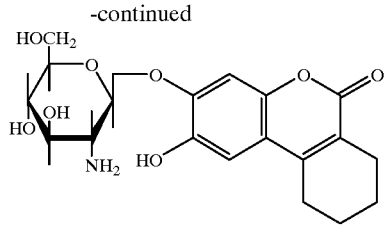

Example 9

Synthesis of 3,4-cyclohexenoesculetin-6(7)-phosphoric Acid

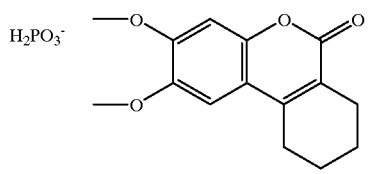

To a stirred solution of 3,4-cyclohexenoesculetin (2.32 g, 10 mmol) in pyridine (5 ml) and toluene (10 ml) was added phosphoryl chloride (1.84 g, 12 mmol) at 0° C. The stirred solution was allowed to warm to room temperature and subsequently heated on an oil bath at 60° C. for 2 hours. The cooled reaction mixture was poured into water with good stirring and made alkaline (pH 12) by addition of 2 M sodium hydroxide solution.

After storage overnight at 5° C., the toluene was removed by dichloromethane extraction and the aqueous layer adjusted to pH 8 with hydrochloric acid and rotary evaporated at 50–60° C. to give a pale yellow residue. This was dissolved in hot water and on cooling to 0° C. the sodium salt of the phosphate separated as an off-white powder TLC (solvent—ethyl acetate/toluene, 3:1) demonstrated mainly baseline material (u.v. absorbing) but with some contaminating esculetin still remaining. This could be largely removed by repeated extraction with ether.

Example 10

Synthesis of N(-7(6)-octanoyloxy-6(7)-hydroxycoumarin-4-acetyl) Glycylglycine

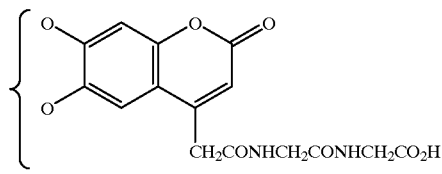

6,7-dihydroxycoumarin-4-acetic acid (2.04 g, 10 mmol) was acetylated by dissolving in excess acetic anhydride (10 ml) and addition of 2–3 drops of sulphuric acid (d=1.84) on gently warming a slight exotherm occurred and after a further 30 minutes at 40° C., the reaction mixture was cooled and poured onto ice/water (100 ml). The white solid which slowly formed was removed by suction filtration and washed with cold water and dried in a vacuum oven at ambient temperature.

The product (diacetate) was not recrystallised but was converted to the acid chloride by addition of thionyl chloride (10 ml) and subsequently remixing for 1 hour. Excess thionyl chloride was removed under reduced pressure and traces eliminated by repeated evaporation with dry ether.

The oily acid chloride was directly dissolved in tetrahydrofuran (20 ml) and introduced in a slow stream into a well stirred solution of glycylglycine (1.32 g, 10 mmol) dissolved in a mixture of water (20 ml) and pyridine (2 ml) to act as base. After 3 hours the solution was rotary evaporated to remove tetrahydrofuran and deprotected by addition of concentrated ammonia (5 ml). After 1 hour, deacetylation was complete and solvents were removed by rotary evaporation under reduced pressure at 50–60° C. The product was contaminated with excess glycylglycine and salts and was therefore recrystallised from methanol/water to give the product N(6,7-dihydroxycoumarin-4-acetyl)glycylglycine.

Esterification

The glycylglycine conjugate (1.68 g, 5 mmol) was dissolved in pyridine (10 ml) and to the stirred solution was added octanoyl chloride (0.9 g, 5.5 mmol) the reaction mixture was stirred at room temperature for 2 hours and then poured into a mixture of ice/water (90 ml) and concentrated hydrochloric acid (10 ml) with efficient stirring. The gummy solid which separated was dissolved in ethyl acetate and washed with concentrated sodium chloride solution. The organic phase was separated, dried (anhydrous sodium sulphate) and rotary evaporated to give a waxy solid of the octanoate ester of the hydrophillic esculetin.

N(7(6)-butyryloxy-6(7)-hydroxycoumarin-4-acetyl) glycylglycine

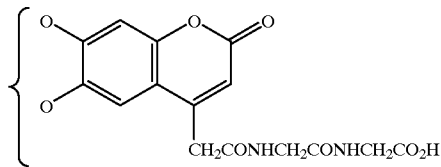

By a similar procedure, but substitution of butyrylchloride (0.58 g, 5.5 mmol) in the esterification process, there was obtained the corresponding butyrate ester (N(7(6)-butyryloxy-6(7)-hydroxycoumarin-4-acetyl)glycylglycine).

Example 11

Test Procedures Using Compounds Previously Synthesised in Examples 1 to 10

Bacteriological investigations were performed on agar plates with glycosides or other derivatives of the modified esculetins incorporated. The following description employing 3,4-cyclohexenoesculetin-β-D-glucoside for differentiation of Gram positive streptococci and related organisms, and for visualisation of esculin-positive colonies serves to illustrate the generic application of these novel compounds.

Esculin agar was prepared as follows; Columbia agar (45 g) Ferric ammonium citrate (0.5 g) and esculin (1.0 g) were dissolved by boiling in distilled water (1 liter) the pH of this medium was then adjusted to 7.5 and the medium sterilised by autoclaving for 10 minutes at 116° C. The medium was allowed to cool to 55° C. before being poured in 20 ml volumes. Agar containing 3,4,-cyclohexenoesculetin-β-D-glucoside was prepared in an identical fashion except that this novel glucoside (CHE-β-D-gluc) (0.5 g) was substituted for esculin.

150 strains of enterococci collected from a wide range of clinical and environmental samples were identified using the scheme of Facklam and Collins (*J. Clinical Microbiol.* 27 731–734 (1989)). Each of these strains was inoculated into physiological saline to produce an inoculum of approximately $10^8$ organisms per ml. This was achieved by performing a comparison with a McFarlane Standard 0.5. Using a multi-point inoculator (Denley), 1 μl of each suspension was then inoculated onto both of the test media ensuing that no more than 12 strains were inoculated per plate. In addition to these enterococci a selection of 40 streptococci and 12 strains of *Listeria sp.* were collected and identified with the API 32 STREP with complimentary tests where indicated. These were also inoculated in identical fashion. 250 strains of Enterobacteriaceae were also collected from a wide range of sources and their identity confirmed by the API 20 E system (Biomerieux). These were inoculated onto both esculin and CHE-β-D-glucoside media as described above.

Finally, 7 strains of enterococci and two strains of streptococci were obtained from the National Collection of Type Cultures (NCTC), London. These were: *Enterococcus faecium* NCTC 7171, *Enterococcus faecalis* NCTC 755, *Enterococcus gallinarum* NCTC 11428, *Enterococcus mundtii* NCTC 12343, *Enterococcus casseliflavus* NCTC 12341, *Enterococcus durans* NCTC 8307, *Enterococcus raffinosis* NCTC 12192, *Streptococcus agalactiae* NCTC 8181 and *Streptococcus bovis* NCTC 8177. Suspensions of these 10 strains were prepared as above at $10^8$ organisms per ml and diluted in sterile distilled water by standard methods to produce suspensions of approximately 1 organism per ml. 3×100 ml volumes of each suspension were then filtered onto 3 cellulose nitrate membrane filters (Sartorius) using a standard filtration method. One of these filters was placed onto a CHE-β-D-glucoside plate, the second onto an esculin plate and the third onto a Columbia agar plate without substrate. All plates were incubated at 37° C. in air for exactly 18 hours, except for the plates inoculated with streptococci which were incubated in air supplemented with 5% carbon dioxide. After incubation plates were examined for the presence of black or brown colonies and colony counts were performed on the membrane filters.

Results

All strains used in this study grew well on both CHE-β-D-glucoside and esculin-containing media. The two substrates were markedly different with respect to their diffusion in the agar. Hydrolysis of esculin resulted in a black complex which diffused widely whereas hydrolysis of CHE-β-D-glucoside produced a black complex highly restricted to the bacterial growth. It can be seen from Table 1 that the hydrolysis of CHE-β-D-glucoside correlated extremely closely with hydrolysis of esculin. This was particularly true of the Gram-positive bacteria where every strain tested showed complete correlation between the two substrates. For example, of 150 strains of enterococci and 12 strains of *Listeria sp.* every strain hydrolysed both esculin and CHE-β-D-glucoside to produce black colonies. Excellent correlation was also achieved between these two substrates for the Gram-negative bacteria tested. One exception to this was in the case of *E. coli* where 4 strains (10%) appeared to hydrolyse CHE-β-D-glucoside but were unable to hydrolyse esculin.

In the membrane filtration experiment all of the NCTC strains of enterococci and the strain of *S. bovis* produced black colonies on CHE-β-D-glucoside medium. On the filters placed on esculin medium all of the strains produced a light brown diffusible complex which spread across the surface of the filter and also into the agar below the membrane. There was no statistical difference between the colony counts on CHE-β-D-glucoside, esculin or brain heart infusion for any of the organisms tested (data not shown). *S. agalactiae* NCTC served as a negative control and did not demonstrate hydrolysis of either substance.

The main advantage of CHE-β-D-glucoside is that when the released cyclohexenoesculetin combines with iron, the resulting black complex is highly insoluble and does not diffuse through the agar medium. This results in the formation of discrete black colonies which can easily be differentiated within a mixed culture. In contrast when esculin is hydrolysed, the released esculetin combines with iron to form a brown/black complex which diffuses rapidly through agar. This diffusion can lead to difficulties in distinguishing esculin-positive colonies within a mixed culture. The different between the two substrates is highlighted in FIG. 1 which shows a strain of *Listeria monocytogenes* (NCTC 11994) on CHE-β-D-glucoside medium and a traditional esculin-based selective agar. The absence of any diffusion of the black complex when using CHE-β-D-glucoside might also provide a considerable advantage when identifying bacteria using a multi-point inoculation technique if large numbers of strains are applied to each plate.

Another highly useful attribute of CHE-β-D-glucoside which has emerged from this study is its potential application in membrane filtration studies for faecal streptococci/ enterococci. Esculin has long been regarded as a potentially useful substrate for such a purpose, however the problems associated with the diffusion of the esculetin complex have not been overcome despite much effort (Daoust et al *Applied Microbiology* 29 584–589 (1975)). This problem of diffusion is particularly acute when large numbers of enterococci are present and the whole membrane is stained with the tan-coloured esculetin-complex (Brodsky et al *Applied and Environmental Microbiology* 31 695–699 (1976)). When CHE-β-D-glucoside is used as the substrate, enterococci grow as discrete black colonies on the membrane which can be easily differentiated within a mixed population. This is because the black complex formed within the colony is unable to diffuse through the membrane and into the agar, hence any colour produced is highly restricted to the actual colony. In the case of esculin, the smaller complex formed readily diffuses through the membrane into the agar and the brown coloration produced is poorly visible due to widespread diffusion. This difference between the two substrates is highlighted in FIG. 2.

It has been reported that hydrolysis of esculin may be rapidly detected by monitoring the disappearance of the natural substrate fluorescence, during hydrolysis in the presence of iron salts (Edberg et al *J. Clinical Microbiology* 4 180–184 (1976)). CHE-β-D-glucoside, unlike esculin, is not fluorescent due to substitution of the 7-hydroxyl group of the cyclohexenoesculetin molecule. However, when this substrate is hydrolysed the cyclohexenoesculetin released is fluorescent. Therefore, an alternative strategy for a fluorescence assay using CHE-β-D-glucoside would be to look for generation of fluorescence in the absence of iron salts. In conclusion, CHE-β-D-glucoside is a highly useful substrate which produces a black non-diffusible product upon hydrolysis by β-D-glucosidase in the presence of iron. The substrate appears to be non-inhibitory and its synthesis is relatively straightforward.

TABLE 1

Hydrolysis of esculin and CHE-glucoside by a variety of bacteria

| | No. of strains | % CHE-GLUCOSIDE Positive | % Esculin Positive |
|---|---|---|---|
| Gram positive species | | | |
| *Enterococcus casseliflavus* | 1 | 100 | 100 |
| *Enterococcus durans* | 2 | 100 | 100 |
| *Enterococcus faecalis* | 83 | 100 | 100 |
| *Enterococcus gallinarum* | 3 | 100 | 100 |
| *Enterococcus raffinosus* | 5 | 100 | 100 |
| *Enterococcus faecium* | 56 | 100 | 100 |
| *Listeria ivanovii* | 2 | 100 | 100 |
| *Listeria monocytogenes* | 10 | 100 | 100 |
| *Streptococcus agalactiae* | 7 | 0 | 0 |
| *Streptococcus bovis* | 10 | 100 | 100 |
| *Streptococcus dysgalactiae* | 2 | 0 | 0 |
| *Streptococcus mitis* | 4 | 0 | 0 |
| *Streptococcus mutans* | 2 | 100 | 100 |
| *Streptococcus oralis* | 4 | 0 | 0 |
| *Streptococcus pneumoniae* | 4 | 0 | 0 |
| *Streptococcus pyogenes* | 2 | 100 | 100 |
| *Streptococcus sanguis* | 5 | 40 | 40 |
| | 202 | | |
| Gram negative species | | | |
| *Citrobacter diversus* | 5 | 100 | 100 |
| *Citrobacter freundii* | 11 | 0 | 0 |
| *Enterobacter aerogenes* | 2 | 100 | 100 |
| *Enterobacter agglomerans* | 1 | 100 | 100 |
| *Enterobacter cloocoe* | 20 | 80 | 80 |
| *Escherichia coli* | 40 | 10 | 0 |
| *Escherichia hermanii* | 1 | 0 | 0 |
| *Hafnia alvei* | 7 | 0 | 0 |
| *Klebsiella oxytoca* | 20 | 100 | 100 |
| *Klebsiella ozaenae* | 1 | 100 | 100 |
| *Klebsiella pneumoniae* | 35 | 100 | 100 |
| *Proteus mirabilis* | 15 | 0 | 0 |
| *Proteus penneri* | 2 | 0 | 0 |
| *Proteus vulgaris* | 5 | 100 | 100 |
| *Providencia rettgeri* | 2 | 50 | 50 |
| *Providencia stuartii* | 7 | 0 | 0 |
| *Salmonella sp.* | 21 | 0 | 0 |
| *Serratia liquefaciens* | 17 | 100 | 100 |
| *Serratia marcescens* | 20 | 100 | 100 |
| *Shigella flexneri* | 2 | 0 | 0 |
| *Shigella sonnei* | 9 | 0 | 0 |
| *Yersinia enterocolitica* | 4 | 0 | 0 |
| *Yersinia pseudotuberculosis* | 3 | 100 | 100 |

Example 12

CHE-glucoside in Blood Agar

Cyclohexenoesculetin-glucoside (CHE-glucoside) was incorporated into Blood agar bases for detection and identification of organisms producing haemolysis and glucosidase. When organisms are incubated anaerobically, CHE-glucoside Blood agar bases can be used to detect the presence of glucosidase producing anaerobic bacteria such as *Bact. fragilis*.

41 grams of Columbia agar base (Lab 1) was weighed and placed in a flask, together with 0.5 grams CHE-glucoside, 0.95 grams ferric gluconate, 0.05 grams zinc acetate. One liter of water was added, mixed and autoclaved at 121° C. for 15 minutes. The flask was cooled to 47° C. and 100 ml of horse blood added mixed and poured into Petri dishes.

Bacteria Tested

*Strept. pyrogenes*—3 strains
*Strept. milleri*—1 strain

*Enterococci spp.*—5 strains
Group C Streptococci—2 strains
*Strep. sanguis*—1 strain
*Ps. aeruginosa*—1 strain
*E. coli*—1 strain
*Clost. perfringens*—1 strain
*Bact. fragilis*—1 strain Results The following strains produced black colonies:
All strains of Enterococci, *Strep. sanguis, Strept. milleri* Group F, *Bact. fragilis*
All strains of *Strept. pyrogenes,* Streptococci belonging to Groups B, C and F, and some Enterococci produced some haemolysis.

In summary, CHE-glucoside incorporated into blood agar bases gives clear detection of glucosidase enzymes with no interference with haemolysis patterns. Using these two indicators and appropriate selective agents these important pathogens can be isolated and provisionally identified on primary culture plates.

We claim:

1. A compound of general formula I:

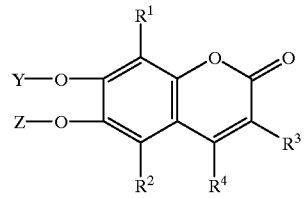

wherein
each of $R^1$ and $R^2$ independently represents a hydrogen or a halogen atom or another group which does not interfere with subsequent iron chelation;
each of $R^3$ and $R^4$ independently represents a $(C_1-C_8)$ alkyl or $(C_6$ or $C_{10})$aryl$(C_1-C_8)$alkyl or an optionally modified carboxyl-bearing group of the general formula —$CH_2(CH_2)_n COX$, where n is a number from 0 to 3 and X represents a hydroxyl group or another hydrophillic group,
and, $R^4$ alternatively represents a hydrogen atom and $R^3$ alternatively represents an acyl group of the general formula —COR, in which R represent a $(C_1-C_8)$alkyl, $(C_6$ or $C_{10})$aryl$(C_1-C_8)$alkyl or $(C_5-C_8)$cycloalkyl group,
provided that $R^3$ and $R^4$ between them contain at least three carbon atoms;
or $R^3$ and $R^4$ together with the carbon atoms to which they are attached form a $(C_5-C_8)$cycloalkene ring; and
one of Y and Z represents an enzymatically cleavable group and the other of Y and Z represents a hydrogen atom;
or a suitable salt or hydrate thereof.

2. The compound as claimed in claim 1, in which:
$R^1$ is chlorine or hydrogen;
$R^2$ is chlorine or hydrogen;
$R^3$ is $(C_1-C_4)$alkyl or benzyl;
$R^4$ is $(C_1-C_4)$alkyl; or —$CH_2(CH_2)_n COX$, where n is a number from 0 to 3 and X represents a hydroxyl group or a hydrophilic substituent selected from the group consisting of:

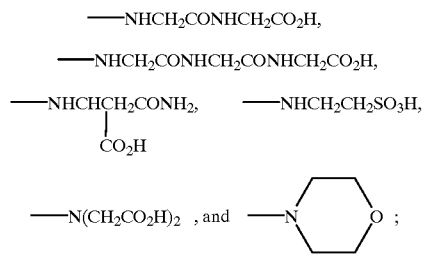

$R^3$ and $R^4$ together with the carbon atoms to which they are attached form a $(C_5-C_8)$ cycloalkene ring; and
the enzymatically cleavable group represented by Y or Z is an α- or β-linked sugar residue or a phosphate or a carboxylate ($R^5COO$—) group, where $R^5$ represents a $(C_1-C_{10})$ alkyl group.

3. The compound of claim 2, wherein said β-linked sugar residue is selected from the group consisting of β-D-glucose, β-D-galactose, β-D-xylose, β-D-glucuronic acid, and N-acetyl-β-D-glucosamine.

4. The compound as claimed in claim 1 which is, 3,4-cyclohexenoesculetin-β-D-galactoside,

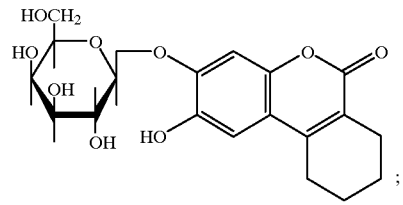

3,4-cyclohexenoesculetin-β-D-glucoside,

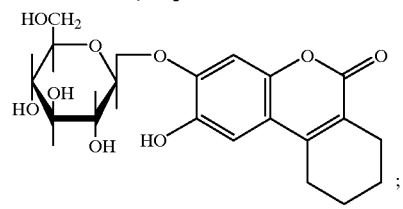

3,4-cyclohexenoesculetin-β-D-glucuronide,

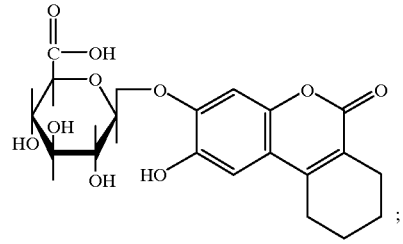

3-benzyl-4-methylesculetin-β-D-glucoside,

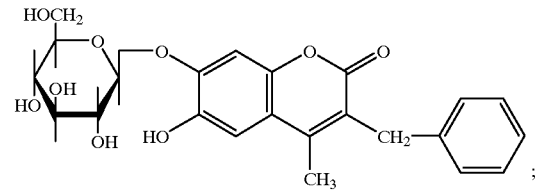

-continued 3,4-cyclohexenoesculetin-N-acetyl-β-glucosaminide,

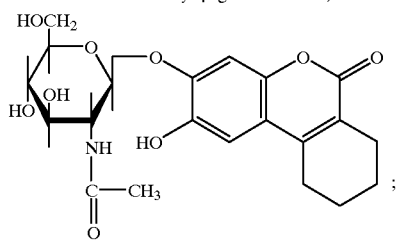

3,4-cyclohexenoesculetin-β-D-xyloside,

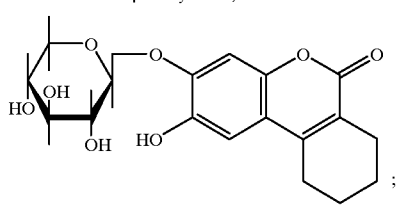

3-n-butyl-4-methylesculetin-β-D-galactoside,

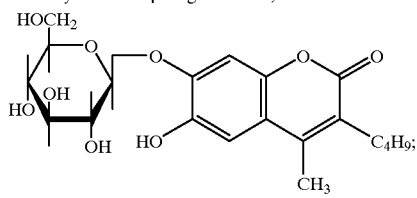

3-n-butyl-4-methylesculetin-β-D-glucoside,

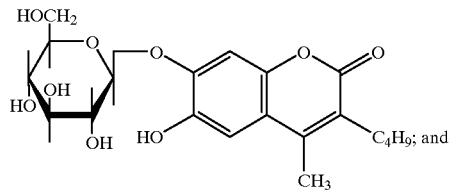

3,4-cyclohexenoesculetin-6(7)-phosphoric acid,

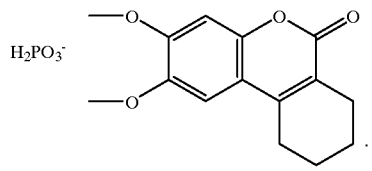

5. A process for the preparation of the compound of claim 1, comprising: derivatising, at position 6 or 7, an optionally protected compound of general Formula II:

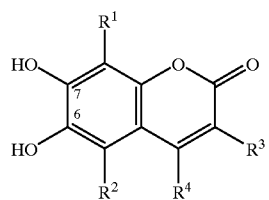

(II)

wherein $R_1$–$R_4$ are defined as in claim 1.

6. The process of claim 1, wherein the means for said derivatising is glycosylation, phosphorylation or esterification.

7. A process for the preparation of a compound of claim 1, wherein Y or Z is an oxidised α- or β-linked sugar residue, comprising:

selecting a compound of claim 1, wherein Y or Z is an oxidisable α- or β-linked sugar residue, and reacting said compound, wherein Y or Z is an oxidisable α- or β-linked sugar residue, with oxygen in the presence of a platinum catalyst and carbon to produce said oxidised compound.

8. A process for the preparation of a compound of claim 1, wherein Y is hydrogen, comprising:

selecting a compound of claim 1, wherein Y is glucose and Z is hydrogen, derivatising the phenolic group at the 6-position, and hydolysing with a glucosidase enzyme, to produce said compound where Y is hydrogen.

9. A composition comprising a compound of claim 1 and a microbiologically acceptable diluent, excipient or substrate.

10. The composition as claimed in claim 9, in which the substrate is a growth support medium.

11. The composition as claimed in claim 10, in which the growth support medium is solid, semi-solid or liquid.

12. The composition as claimed in claim 10, in which the growth support medium is agar.

13. The composition as claimed in claim 10, in which the growth support medium additionally comprises one or more of an essential nutrient, mineral, vitamin or antibiotic.

14. A culture dish containing a microbiologically useful amount of the composition as claimed in claim 9.

15. A method for the detection or identification of a micro-organism in a sample, comprising the steps of:

(a) growing the micro-organism isolated from the sample on a growth support medium containing the compound of claim 1, and (b) detecting the release of an identifiable colored or fluorescent marker following the hydrolysis of said compound of claim 1.

16. The method as claimed in claim 15, wherein the sample is a biological sample, edible substance, water or other potable liquid.

17. The method as claimed in claim 16, wherein the biological sample is saliva, urine, blood, faeces, the contents of the stomach or a biopsy sample.

18. A kit comprising a growth medium wherein said growth medium comprises the compound of claim 1.

19. The kit of claim 17 further comprising a culture dish.

* * * * *

UNITED STATES PATENT AND TRADEMARK OFFICE
CERTIFICATE OF CORRECTION

PATENT NO. : 6,008,008
DATED : December 28,1999
INVENTOR(S) : James et al.

It is certified that error appears in the above-identified patent and that said Letters Patent is hereby corrected as shown below:

On the Title Page after the entry which contains the filing date of the application which issued as the present patent and before "Foreign Application Priority Data," please insert the following entry:

--Related U.S. Application Data

Continuation of application No. PCT/GB97/01202, May 1, 1997.--

On the facing page, under "Foreign Application Priority Data," change "9609024" to --9609024.6--.

In column 26, line 1, in claim 6, change "claim 1" to --claim 5--.

Signed and Sealed this

Twenty-seventh Day of March, 2001

Attest:

NICHOLAS P. GODICI

Attesting Officer

Acting Director of the United States Patent and Trademark Office